United States Patent [19]
Simon

[11] Patent Number: 4,886,733
[45] Date of Patent: Dec. 12, 1989

[54] PHOTOGRAPHIC PRODUCTS AND PROCESSES

[75] Inventor: Myron S. Simon, West Newton, Mass.

[73] Assignee: Polaroid Corporation, Cambridge, Mass.

[21] Appl. No.: 252,661

[22] Filed: Oct. 3, 1988

[51] Int. Cl.[4] .......................... G03C 5/54; G03C 5/26; C07D 311/78

[52] U.S. Cl. .................................... 430/221; 430/236; 430/449; 430/486; 430/487; 549/281; 549/283; 549/290

[58] Field of Search ............... 430/221, 236, 486, 487, 430/449; 549/281, 290, 283

[56] References Cited

U.S. PATENT DOCUMENTS

| | | | |
|---|---|---|---|
| 3,415,644 | 12/1968 | Land | 430/220 |
| 3,415,645 | 12/1968 | Land | 430/220 |
| 3,415,646 | 12/1968 | Land | 430/220 |
| 3,647,437 | 3/1972 | Land | 430/221 |
| 3,702,244 | 11/1972 | Bloom et al. | 430/221 |
| 3,702,245 | 11/1972 | Simon et al. | 430/221 |
| 4,456,674 | 6/1984 | Cerankowski et al. | 430/221 |

*Primary Examiner*—Richard L. Schilling
*Attorney, Agent, or Firm*—Sybil A. Campbell

[57] ABSTRACT

This invention relates to diffusion transfer photographic processes adapted to be performed in the presence of ambient light and to diffusion transfer products useful in such processes wherein unexpectedly enhanced opacification in the red and near infrared region of the visible spectrum is achieved by employing phenanthrol/carboxynaphthol phthaleins as the light-absorbing, pH-sensitive optical filter agent for the longer wavelength region of the visible spectrum.

23 Claims, 1 Drawing Sheet

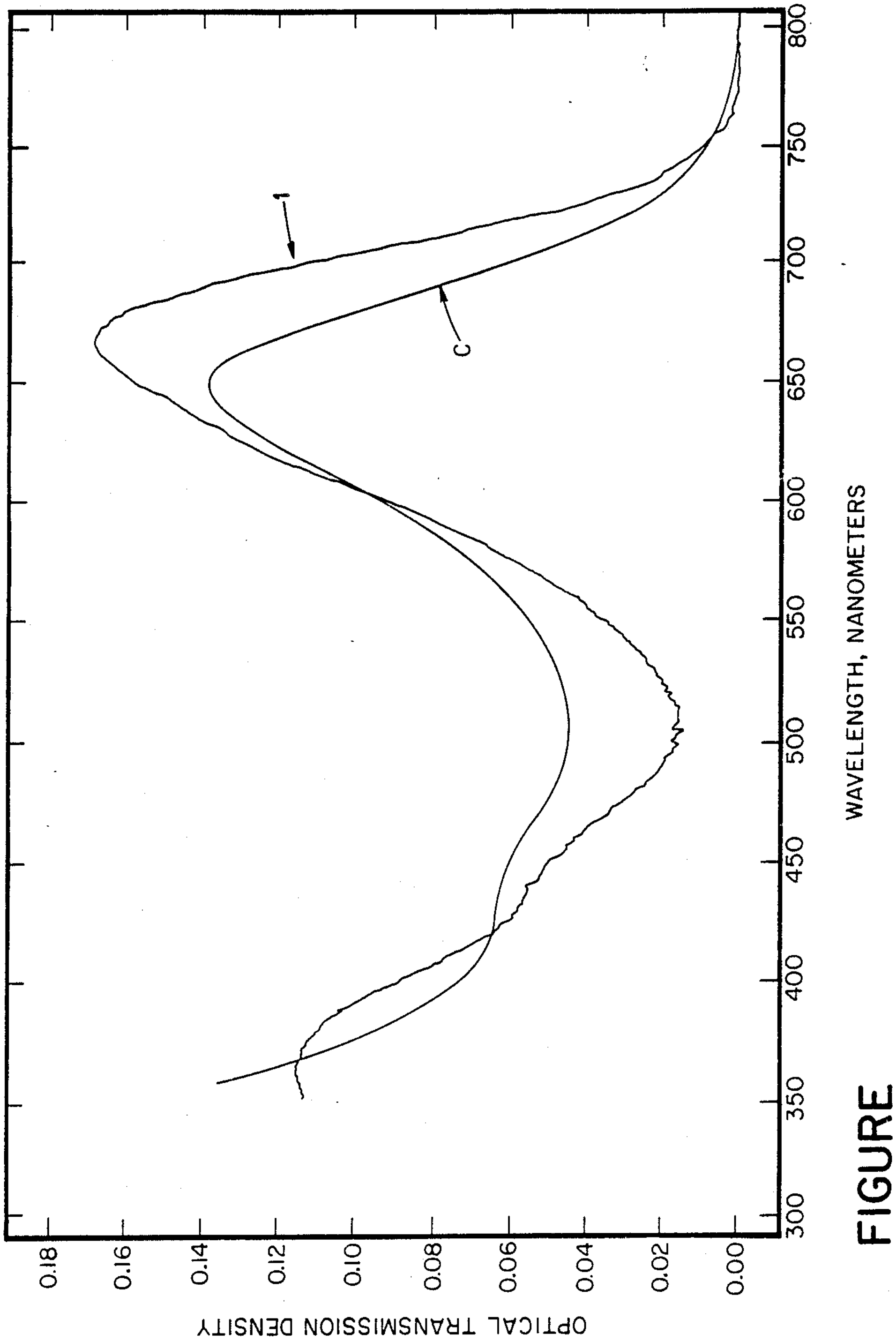
FIGURE

PHOTOGRAPHIC PRODUCTS AND PROCESSES

BACKGROUND OF THE INVENTION

This invention relates to photography, and more particularly, it relates to photographic processes performed in ambient light and to photographic products useful in such processes.

A number of diffusion transfer processes for producing photographic images in both black-and-white and in color are now well known. Of particular interest are diffusion transfer processes wherein the image-receiving layer carrying the transfer image is not separated from the developed photosensitive layer(s) after processing but both components are retained together as a permanent laminate. Included as part of the laminate is a layer of a light-reflecting material, preferably titanium dioxide, positioned between the image-carrying layer and the developed photosensitive layer(s). The light-reflecting layer separating the image-carrying and photosensitive components provides a white background for the transfer image and masks the developed photosensitive layer(s). In addition to these layers, the laminate usually includes dimensionally stable outer layers or supports, at least one of which is transparent so that the resulting transfer image may be viewed by reflection against the background provided by the light-reflecting layer. Diffusion transfer processes for forming images viewable without separation of the photosensitive and image-receiving components and film units useful in such processes are described, for example, in U.S. Pat. Nos. 3,415,644, 3,415,645 and 3,415,656 issued Dec. 10, 1968 to Edwin H. Land.

U.S. Pat. No. 3,647,437 issued Mar. 7, 1972 to Edwin H. Land also is concerned with diffusion transfer processes wherein the resulting photograph comprises the developed photosensitive layer(s) retained with the image-receiving layer as part of a permanent laminate. In the processes disclosed in this patent, a photographic film unit comprising a photosensitive element is developed in ambient light but further undesired exposure during processing is prevented by a light-absorbing material or optical filter agent which is retained in the processed film unit. In a preferred embodiment, the optical filter agent is a pH-sensitive dye, i.e., a dye possessing spectral absorption characteristics that are reversibly alterable in response to changes in environmental pH and particularly, a pH-sensitive dye having a colored or light-absorbing form above a given alkaline pH and a colorless or non-light-absorbing form below said pH. In a particularly preferred embodiment, the film unit is of the type described in aforementioned U.S. Pat. No. 3,415,644 and comprises a first sheet-like component comprising an opaque support carrying a silver halide emulsion layer(s) and a second sheet-like component comprising a transparent support carrying an image-receiving layer which are in fixed relationship prior to exposure, which relationship is maintained after processing. After photoexposure through said transparent support, an aqueous alkaline processing composition is distributed in a thin layer between said components. The processing composition contains a light-reflecting pigment and at least one pH-sensitive dye which is in its colored form at the initial pH of said aqueous alkaline processing composition and which, after at least the initial stages of processing, is converted to its colorless form by reducing the environmental pH, for example, by including an acid-reacting layer as part of the film unit. The concentrations of the light-reflecting pigment and light-absorbing optical filter agent required to provide adequate protection of the -photosensitive layer(s) will vary with the process being performed and the anticipated conditions, e.g., light intensity, dark time, etc. Preferably, the concentrations of these materials are such that the processing composition layer containing the pigment and optical filter agent will have a transmission density of at least about 6 but a reflection density not greater than about 1.

Various pH-sensitive dyes have been disclosed as light-absorbing optical filter agents for protecting a selectively exposed photosensitive material from post-exposure fogging in the presence of extraneous incident light. Examples of pH-sensitive dyes that have been found particularly useful are the phthaleins, i.e.,the phthalide and naphthalide dyes derived from indoles disclosed in U.S. Pat. No. 3,702,244 issued Nov. 7, 1972 to Stanley M. Bloom, Alan L. Borror, Paul S. Huyffer and Paul T. MacGregor, and the phthalide and naphthalide dyes derived from phenols and 1- napthols disclosed in U.S. Pat. No. 3,702,245 issued Nov. 7, 1972 to Myron S. Simon and David P. Waller. As discussed in the latter patent, phenol and 1-naphthol phthaleins especially useful for photographic processes employing highly alkaline media are those possessing a hydrogen-bonding group, for example, a carboxy group ortho to the p-hydroxy group of the phenol or naphthol radicals. These phthaleins also may contain other substituents, and as discussed in column 7, lines 40 to 64, the hydrogen-bonding or other substituent may comprise a fused ring. For example, the phenol or naphthol radicals may contain as a fused substituent, a fused cycloaliphatic or aromatic ring usually having 5 or 6 members which ring may be carbocyclic or heterocyclic and unsubstituted or substituted. As an illustration, fused rings may be employed to give a hydrogen-bonded radical such as 8-hydroxy-5-quinolyl, 5- hydroxy-4-azaphenanthren-8-yl and a phenanthrol radical substituted in the peri position with, e.g., hydroxy. As discussed in these and other patents, the 1-naphthol or phenol phthaleins generally are used in combination with the indole phthaleins where it is desired to provide protection from post-exposure fogging throughout the visible spectrum.

U.S. Pat. No. 4,456,674 issued June 26, 1984 to Leon D. Cerankowski, Gary S. LaPointe and Neil C. Mattucci discloses enhanced opacification systems employing metal cations for complexing with phthalein optical filter agents and in one embodiment discloses the use of an alkali earth metal salt to increase the light-absorbing ability of a carboxynaphthol phthalein within the layer of processing composition.

SUMMARY OF THE INVENTION

According to the present invention, it has been found that phenanthrol/o-carboxynaphthol phthaleins provide unexpectedly enhanced protection against post-exposure fogging in the red and near infrared region of the visible spectrum. In the comparison to di-(o-carboxynaphthol) phthaleins, see FIGURE, the subject phthaleins possess an absorption spectrum that extends into the far red and near infrared and absorb incident radiation more strongly at the longer wavelengths. Because of this enhanced absorption, which could not be predicted on the basis of the earlier phthaleins, the subject phthalein optical filter agents allow the use of thinner layers of pigmented reagent and/or more efficient use, i.e., lesser concentrations of optical filter agent without requiring the addition of metal salts or other material to provide added protection in the longer wavelength range.

It is, therefore, the primary object of the present invention to provide diffusion transfer photographic products and processes employing as the processing composition, an aqueous alkaline solution of a light-reflecting pigment and a phenanthrol/o-carboxynaphthol phthalein as at least one light-absorbing pH-sensitive optical filter agent.

It is another object of the present invention to provide photographic products and processes of the foregoing type wherein the processing composition additionally includes a light-absorbing, pH-sensitive indole phthalein optical filter agent.

It is a further object of the present invention to provide phenanthrol/o-carboxynaphthol phthaleins useful as light-absorbing, pH-sensitive optical filter agents.

Other objects of this invention will in part be obvious and will in part appear hereinafter.

The invention accordingly comprises the processes involving the several steps and the relation and order of one or more of such steps with respect to each of the others, and the products possessing the features, properties and relation of elements which are exemplified in the following detailed disclosure, and the scope of the application of which will be indicated in the claims.

For a fuller understanding of the nature and objects of the invention, reference should be had to the following detailed description taken in conjunction with the accompanying drawing.

BRIEF DESCRIPTION OF THE DRAWING

The Figure is a graphic illustration comparing the spectral absorption characteristics of the phthalein optical filter agent of Example 1 of the present invention designated Curve 1 with the spectral absorption characteristics of a di-(o-carboxynaphthol) phthalein optical filter agent (Curve C). These curves represent the optical transmission density, i.e., the absorbance of the respective optical filter agents measured over the wavelength range of 350 nm to 800 nm in aqueous alkaline solution.

DETAILED DESCRIPTION OF THE INVENTION

As noted above, it has been found that enhanced opacification of a pigmented processing composition layer and, particularly, added protection in the red and near infrared region of the visible spectrum can be achieved by employing phenanthrol/o-carboxynaphthol phthaleins as the light-absorbing, pH-sensitive sensitive optical filter agent for the longer wavelength region of the visible spectrum. As used herein the term "phthalein" is intended to include both phthalides and naphthalides. These phthaleins may be represented by the formula

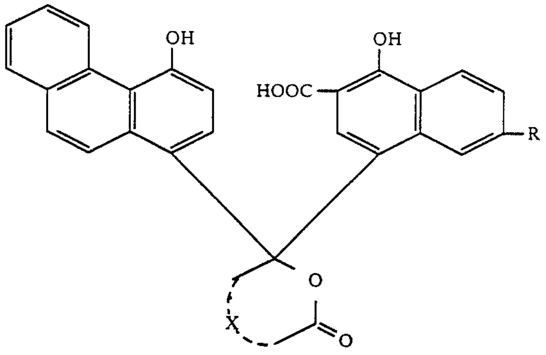

wherein R is alkoxy having at least 12 carbon atoms and X represents the carbon atoms necessary to complete phthalide or naphthalide. The respective phthalide and naphthalide moieties are represented by the following formulae:

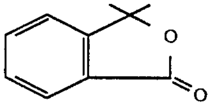

and

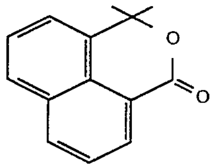

Preferably, X completes naphthalide.

Illustrative R substituents include branched or straight chain alkoxy having at least 12 carbon atoms and usually having 12 to 24 carbon atoms such as hexadecyloxy, octadecyloxy, eicosanyloxy and docosanyloxy.

The subject phthaleins may be prepared using any of the various methods previously disclosed for synthesizing phthalides and naphthalides such as that described in U.S. Pat. No. 3,931,228. A preferred method is described in U.S. Pat. No. 3,869,473 and comprises reacting a 3-acyloxy-3-(3-lower carboalkoxy-4'-hydroxy-1'-naphthyl) naphthalide and the phenanthrol in the presence of basic such as pyridine to form the corresponding dye precursor which is then hydrolyzed to yield the corresponding dye product. The 3-acyloxy compounds employed in the above-described method are known and may be prepared according to the procedure disclosed in U.S. Pat. No. 3,806,523.

The following examples are given to illustrate the invention and are not intended to limit the scope thereof.

EXAMPLE 1

Preparation of the compound having the formula

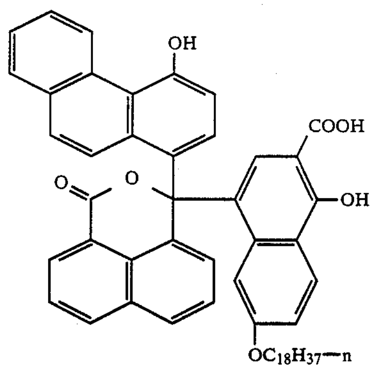

(1) To 20 ml of dry benzene was added 2.0 ml of 3-acetoxy-3-(3carbomethoxy-4-hydroxy-7'-n-octadecyloxy-1'-naphthyl) naphthalide and 0.546 gm of 4-phenanthrol. This mixture was stirred under nitrogen; 1.3 ml of benzene containing pyridine (0.3 ml of pyridine per 50 ml of benzene) was added; and the solution was refluxed for 6½ hours. The reaction mixture was cooled to room temperature and evaporated to a tan solid. The solid was then chromatographed on a silica gel column made with hexane and eluted with a 1:1 hexane/dichloromethane solution to remove a high $R_f$ impurity. Then the column was eluted with 3:7 hexane/dichloromethane solution to obtain the desired dye precursor. The solution was evaporated to a glass and oven dried at 60° C. for 4 hours to give 0.650 gm of the methyl ester dye precursor as a tan solid. m/e 845.

(2) 0.620 gm of the methyl ester dye precursor was suspended in 40 ml of isopropanol under nitrogen and 40 ml of 10% aqueous sodium hydroxide was added. The blue solution was heated under nitrogen with stirring for 2½ hours. The solution was cooled to room temperature and poured with stirring into a solution of 80 ml of distilled water containing 3 ml of acetic acid and 4 ml of conc. hydrochloric acid and stirred for 0.5 hours. The off-white precipitate was filtered off, washed with 300 ml of distilled water and dried at 60° C. in vacuo for 4 hours to give 0.460 gm of 3(4'-hydroxy-1'-phenanthryl)-3-(3"-carboxy-4"-hydroxy-7"-n-octadecyloxy1"-naphthyl) naphthalide as an off-white solid. m/e 831; m.p. 144°-145° C.; λmax 662 (Epsilon=17,000) in 1N KOH.

The 3-acetoxy-3-(3-carbomethoxy-4'-hydroxy-7'-n-octadecyloxy-1'-naphthyl) naphthalide used in Example 1 was synthesized as follows:

(a) 2.0 gms of naphthalic anhydride was added to 30 ml of tetrachloroethane and 3.15 gms of phosphorous pentachloride was added. The mixture was heated at reflux under nitrogen for six hours. The amber solution was cooled to 10° C. and 3.15 gms of $AlCl_3$ was added in several increments over a 20 minute period to give a yellow slurry. Then at 15° C., 4.7 gms of methyl 1-hydroxy-6-octadecyloxy-2-naphthoate dissolved in 50 ml of tetrachloroethane was added dropwise over 0.5 hour. The purple solution was then allowed to warm up to room temperature and stirred for seventeen hours. The solution was poured into 200 ml of crushed ice with stirring. The flask was washed with 60 ml of dichloromethane and combined with the tetrachloroethane/ice mixture. The mixture was then heated on a steam bath until boiling, cooled to room temperature and the organic layer separated, dried with $MgSO_4$, and filtered. 600 ml of hexanes was added to the organic solution and the solution cooled overnight in the freezer. The off-white solid was filtered off, washed with hexanes and air dried to yield 5.34 gms. The solid was then recrystallized from 200 gms acetic acid, filtered, and vacuum dried at 60° C. to yield 4.8 gms of 3-hydroxy-3-(3'-carbomethoxy-4'-hydroxy-7'-n-octadecyloxy-1'-naphthyl) naphthalide as a white solid. m.p. 108°-110° C. λmax 262 (Epsilon=45,300) in ethanol.

(b) To 3.0 gms of 3-hydroxy-3-(3'-carbomethoxy-4'-hydroxy-7'-n-octadecyloxy-1-naphthyl) naphthalide was added 2.7 ml of acetic acid and heated to 80° C. Then 1.8 ml of acetic anhydride was added and the solution heated to 110° C. for 2 hours with stirring. 6 ml of toluene was then added and the solution cooled to 10° C. The off-white precipitate was filtered off and dried at 45° C. in vacuo for 3 hours to give 2 gms of the desired 3-acetoxy-3-(3'-carbomethoxy-4'-hydroxy-7'-n-octadecyloxy-1-naphthyl) nahthalide. m.p. 132°-135° C.

EXAMPLE 2

Preparation of the compound having the formula

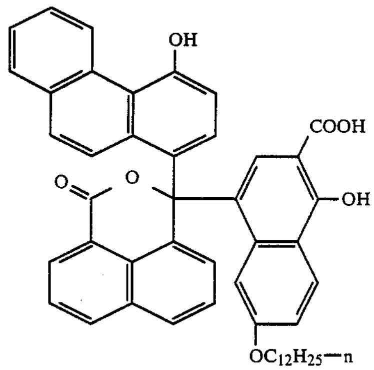

(1) To 25 ml of dry benzene was added 2.00 gms of 3-acetoxy 3-(3'-carbomethoxy-4'-hydroxy -7'-dodecyloxy-1'-naphthyl) naphthalide and 0.619 gm of 4-phenanthrol. This mixture was stirred under nitrogen, 1.3 ml of benzene containing pyridine (0.6 ml of pyridine per 50 ml of benzene) was added and the resulting solution was refluxed under nitrogen for 6 hours. The reaction mixture was evaporated to a tan solid. The solid was then chromatographed on a silica gel column made with hexane and eluted with a 1:1 hexane/dichloromethane solution. Chromatography separated a high $R_f$ impurity (thin layer chromatography using 3:7 hexane/dichloromethane). Then the column was eluted with 1:3 hexane/dichloromethane to obtain the desired product ($R_f$~0.38). Evaporation gave an off-white solid which was vacuum dried at 60° C. for 4 hours to yield 0.490 gm of the dye precursor product. m/e 761.

(2) 0.460 gm of the methyl ester dye precursor was suspended in 30 ml of isopropanol under nitrogen and 36 ml of 10% aqueous sodium hydroxide was added. The blue solution was then heated with stirring to 45° C. for 5.5 hours. The cooled solution was poured into 80 ml of distilled water containing 3 ml of acetic acid and 4 ml of conc. hydrochloric acid and stirred for 0.5 hour. The light tan solid that precipitated was filtered, washed with 300 ml of water and dried in a vacuum oven for 3 hours at 60° C. The solid was then chromatographed on a silica gel column with dichloromethane followed by 1:1 acetone/dichloromethane to give 0.310 gm of the title compound as an off-white solid. m/e 747; m.p. 174°-175° C.; λmax 662 nm (Epsilon=16,600) in 1N KOH.

The 3-acetoxy-3-(3'-carbomethoxy-4'-hydroxy-7'-n-dodecyloxy-1'-naphthyl) naphthalide used in Example 2 above was synthesized as follows:

(a) 3.13 gms of naphthalic anhydride was added to 40 ml of tetrachloroethane and 4.93 gms of phosphorous pentachloride was added. The mixture was heated at reflux under nitrogen for six hours. The amber solution was cooled to 15° C. and 2.10 gms of $AlCl_3$ was added in several increments over a 20 minute period to give a yellow slurry. 6.10 gms of methyl 1-hydroxy-6-dodecyloxy-2-naphthoate dissolved in 60 ml of tetrachloroethane was added dropwise. The purple solution was then allowed to warm up to room temperature and stirred for eighteen hours. The solution was poured into 300 ml of crushed ice with stirring. The flask was washed with 50 ml dichloromethane and combined with the tetrachloroethane/ice mixture. The mixture was heated on a steam bath until boiling, then cooled to room temperature and the organic layer separated, dried with $MgSO_4$, and filtered. 600 ml of hexanes was added to the organic solution and the solution cooled overnight in the freezer. The off-white solid was filtered off, washed with hexanes and air dried to yield 7.6 gms of crude product. The solid was then recrystallized from 200 ml of acetic acid, filtered and vacuum dried to yield 5.35 gms of the desired product. m/e=586. m.p. 124°-126° C.

(b) To 2.0 gms of 3-hydroxy-3-(3'-carbomethoxy-4'-hydroxy-7'-n-dodecyloxy-1'-naphthyl) naphthalide prepared in step (a) was added 3 ml of acetic acid and heated to 90° C. Then 2 ml of acetic anhydride was added and the solution heated for 1.5 hours. The solution was cooled to room temperature and 20 ml of toluene added and then cooled in ice bath to 5° C. Filtration gave an off-white solid which was vacuum dried to give 2.0 gms of the desired 3-acetoxy-3-(3'-carbomethoxy-4'-hydroxy-7'-n-dodecyloxy-1'-naphthyl) naphthalide.

4-phenanthrol was prepared as follows:

(i) To 900 ml of dichloromethane contained in a 3 liter, 3-neck flask equipped with a mechanical stirrer, drying tube and thermometer and surrounded by an ice water bath was added 290.0 g (2.26 moles) naphthalene. To the stirred suspension was added 145.2 g (1.44 moles) of succinic anhydride. A total of 400 g of aluminum chloride was then added in small increments over the next 4½ hours while stirring and cooling in an ice water bath. The resulting amber brown-yellow reaction mixture was stirred at room temperature overnight. Next morning it was poured on crushed ice and acidified with conc. hydrochloric acid. The aqueous portion was decanted and the organic layer was filtered to collect white solids. The solids were washed with dichloromethane containing 20% hexanes and slurried in 700 ml of boiling ethyl acetate. After cooling in a cold water bath, the solids were collected by filtration and washed with fresh ethyl acetate. Then the solids were recrystallized from 500 ml of glacial acetic acid and dried under vacuum to give 195.0 g (59.4% yield) of 4-(2naphthyl)-4-oxobutyric acid as an off-white solid. M.P. 171°-175° C.; M/e 229; λmax 282 nm (7,260) in ethanol.

(ii) To 300 ml of triethylene glycol contained in a 1-liter, 3-neck flask equipped with a magnetic stirrer, thermometer and take-off condenser was added 77.0 g (0.34 mole) of 4-(2-naphthyl)-4-oxobutyric acid, 61.2 g (1.09 moles) potassium hydroxide pellets and 45.44 ml of hydrazine monohydrate. The reaction mixture was heated up to 100°-110° C. with stirring and held there for 90 minutes. The temperature was gradually increased to 195° C. over 4 hours. Strong gas evolution commenced at about 130° C with some distillate coming over above 140° C. The reaction mixture was allowed to cool and then stirred at room temperature overnight. Next morning the reaction mixture was diluted with ice water and while cooling in ice was acidified with conc. hydrochloric acid. The white solids were collected by filtration, washed with warm water and air-dried to yield 69.0 g (94.9% by weight yield) of γ-(2-naphthyl) butyric acid. M.P. 96°-99° C.; M/e 214; λmax 276 (5,580) ethanol.

(iii) To 300 ml of methane-sulfonic acid contained in a 1 liter, 3-neck flask equipped with thermometer, drying tube and magnetic stirring bar was added 82.0 g (0.38 mole) of γ-(2-naphthyl)butyric acid as prepared above and the reaction mixture was heated at 90°-95° C. for one hour with vigorous stirring. The yellow reaction mixture was cooled, poured on crushed ice and extracted with two 350 ml portions of ethyl acetate. The combined organic portions were washed with 5% aqueous sodium hydroxide, water, dried over anhydrous sodium sulfate and then treated with some silica gel powder and Norit A charcoal before filtering. Upon removing the solvent an off-white solid was obtained. Recrystallization from 375 ml of hexane containing 7-10 ml of chloroform gave an oil that solidified to yield 55.0 g (73.3% by weight) of 1,2,3,4-tetrahydro-4-phenanthrone as an off-white solid. M.P. 64°-66° C.; λmax 312 nm (7,510) ethanol; T.L.C. $CH_2Cl_2$. $R_f$=.7.

(iv) In a 1000 ml 3-neck flask equipped with magnetic stirrer and reflux condenser with nitrogen inlet, 400 ml of carbon tetrachloride was added followed by 26 gms of 4 oxo-1,2,3,4-tetrahydrophenanthrene and 26.5 gm of N-bromo succinimide. The reaction was illuminated with a 600 watt Quartzlite lamp for 6 hours. Then an additional 2.0 gms of N-bromosuccinimide was added and the reaction refluxed for 1 hour. The reaction was cooled to room temperature and the solids filtered off and washed with carbon tetrachloride and air dried. The solids were recrystallized from 220 ml of ethyl acetate, filtered and washed with several portions of warm water, dried in vacuo in the presence of $P_2O_5$ to yield 8.3 gms (32.25% by weight) of 4-phenanthrol. m.p. 114°-116° C. m/e 194.

As noted above, the present invention is particularly adapted for facilitating processing outside of a camera of diffusion transfer units which are maintained as a permanent integral laminate after processing, the final transfer image being viewed through one face of the laminate. In such film units a light-reflecting layer is disposed between the developed photosensitive layers and the layer carrying the transfer dye image. These essential layers preferably are confined between a pair of dimensionally stable outer supports, at least one of which is transparent to permit viewing of the transfer dye image by reflection against the background provided by the reflecting layer.

Image dye-providing materials which may be employed generally may be characterized as either (1) initially soluble or diffusible in the processing composition but are selectively rendered non-diffusible in an imagewise pattern as a function of development; or (2) initially insoluble or non-diffusible in the processing composition but which are selectively rendered diffusible or provide a diffusible product in an imagewise distribution as a function of development. These materials may be complete dyes or dye intermediates, e.g., color couplers. The requisite differential in mobility or solubility may, for example, be obtained by a chemical action such as a redox reaction, a coupling reaction or a silver ion assisted cleavage reaction.

Examples of initially soluble or diffusible materials and their application in color diffusion transfer processes are disclosed, for example, in U.S. Pat. Nos. 2,968,554; 2,983,606; 3,087,817; 3,185,567; 3,230,082; 3,345,163; and 3,443,943. Examples of initially non-diffusible materials and their use in color transfer systems are disclosed in U.S. Pat. Nos. 3,185,567; 3,443,939; 3,443,940; 3,227,550; 3,227,552 and 4,076,529. Both types of image dye providing substances and film units useful therewith also are discussed in the aforementioned U.S. Pat. No. 3,647,437 to which reference may be made.

A particularly useful system for forming color images by diffusion transfer is that described in U.S. Pat. No. 2,983,606, employing dye developers (dyes which are also silver halide developing agents) as the image dye-providing materials. In such systems, a photosensitive element comprising at least one silver halide layer having a dye developer associated therewith (in the same or in an adjacent layer) is developed by applying an aqueous alkaline processing composition. Development of exposed silver halide results in oxidation of the dye developer to provide an oxidation product which is appreciably less diffusible than the unreacted dye developer, thereby providing an imagewise distribution of diffusible dye developer in terms of unexposed areas of the silver halide layer, which imagewise distribution is then transferred, at least in part, by diffusion, to a dyeable stratum to impart thereto a positive dye transfer image.

Another system that is particularly useful for forming color images by diffusion transfer is that described in U.S. Pat. No. 4,740,448, which uses the aforementioned dye developer chemistry to form at least one color record and the image dye-releasing thiazolidine chemistry of U.S. Pat. No. 3,719,489 to form at least one of the other color records.

In such color diffusion transfer systems, color transfer images are obtained by exposing a photosensitive element, sometimes referred to as a "negative component", comprising at least a light-sensitive layer, e.g., a gelatino silver halide emulsion layer, having an image dye-providing material associated therewith in the same or in an adjacent layer, to form a developable image; developing this exposed element with a processing composition to form an imagewise distribution of a diffusible image dye-providing material; and transferring this imagewise distribution, at least in part, by diffusion, to a superposed image-receiving layer, sometimes referred to as a "positive component", comprising at least a dyeable stratum to provide a color transfer image. The negative and positive components initially may be carried on separate supports which are brought together during processing and thereafter retained together as the final integral negative-positive reflection print, or they may initially comprise a unitary structure, e.g., integral negative-positive film units of the type described in aforementioned U.S. Pat. No. 3,415,644 wherein the negative and positive components are physically retained together in superposed relationship prior to, during and after image formation. (Procedures for forming such film units wherein the positive and negative components are temporarily laminated together prior to exposure are described, for example, in U.S. Pat. No. 3,652,281 to Albert J. Bachelder and Frederick J. Binda and in U.S. Pat. No. 3,652,282 to Edwin H. Land, both issued Mar. 28, 1972.) In either instance, the positive component is not removed from the negative component for viewing purposes. These components may be laminated together or otherwise secured together in physical juxtaposition.

Film units intended to provide multicolor images comprise two or more selectively sensitized silver halide layers each having associated therewith an appropriate image dye-providing material providing an image dye having spectral absorption characteristics substantially complementary to the light by which the associated silver halide is exposed. The most commonly employed negative components for forming multicolor images are of the tripack structure and contain blue-, green- and red-sensitive silver halide layers each having associated therewith in the same or in a contiguous layer a yellow, a magenta and a cyan image dye-providing material, respectively. Interlayers or spacer layers may be provided between the respective silver halide layers and associated image dye-providing materials or between other layers. Indeed, a light-reflecting spacer layer disposed between a silver halide layer and the associated layer of image dye-providing material may be used to increase effective film speed as a result of the reflection of light back to the silver halide. Particularly suitable light-reflecting spacer layers comprise a light-reflecting pigment dispersed with inert polymeric particles which are substantially non-swelling in alkali and substantially non-film-forming. Such layers form the subject matter of published European Patent Application No. 0066341 published Dec. 8, 1982.

In addition to the aforementioned layers, such film units further include means for providing a reflecting layer between the dyeable stratum and the negative component in order to mask effectively the silver image or images formed as a function of development of the silver halide layer or layers and also to mask image dye-providing material which is not transferred, thereby providing a background, preferably white, for viewing the color image formed in the dyeable stratum, without separation, by reflected light. Preferably, this reflecting layer is provided by including the reflecting agent in the processing composition. The dye transfer image is then viewable against the reflecting layer through a dimensionally stable protective layer or support. As noted above, most preferably another dimensionally stable layer or support is positioned on the opposed surface of the essential layers so that the aforementioned essential layers are between a pair of dimensionally stable layers or support members, one of which is transparent to permit viewing therethrough of the color transfer image. A rupturable container of known description contains the requisite processing composition and is adapted upon application of pressure to release its contents for development of the exposed film unit, e.g., by distributing the processing composition in a substantially uniform layer between the negative and positive components.

The dye developers (or other image dye-providing substances) are preferably selected for their ability to provide colors that are useful in carrying out subtractive color photography, that is, the previously mentioned cyan, magenta and yellow. They may be incorporated in the respective silver halide emulsion or, in the preferred embodiment, in a separate layer behind the respective silver halide emulsion. Thus a dye developer may, for example, be in a coating or layer behind the respective silver halide emulsion and such a layer of dye developer may be applied by use of a coating solution containing the respective dye developer distributed, in a concentration calculated to give the desired coverage of dye developer per unit area, in a film-forming natural, or synthetic, polymer, for example, gelatin, polyvinyl alcohol, and the like, adapted to be permeated by the processing composition.

Dye developers, as noted above, are compounds which contain the chromophoric system of a dye and also a silver halide developing function. By "a silver halide developing function" is meant a grouping adapted to develop exposed silver halide. A preferred silver halide development function is a hydroquinonyl group. Other suitable developing functions include ortho-dihydroxyphenyl and ortho- and para-amino substituted hydroxyphenyl groups. In general, the development function includes a benzenoid developing function, that is, an aromatic developing group which forms quinonoid or quinone substances when oxidized.

The image-receiving layer may comprise any of the materials known in the art, such as polyvinyl alcohol, gelatin, etc., preferably containing a mordant for the transferred image dye(s). If the color of the transferred image dye(s) is affected by changes in pH, the pH of the image layer may be adjusted to provide a pH affording the desired color.

In the various color diffusion transfer systems which have previously been described and which employ an aqueous alkaline processing fluid, it is well known to employ an acid-reacting reagent in a layer of the film unit to lower the environmental pH following substantial dye transfer in order to increase the image stability and/or to adjust the pH from the first pH at which the image dyes are diffusible to a second (lower) pH at which they are not. For example, the previously mentioned U.S. Pat. No. 3,415,644 discloses systems wherein the desired pH reduction may be effected by providing a polymeric acid layer adjacent the dyeable stratum. Thee polymeric acids may be polymers which contain acid groups, e.g., carboxylic acid and sulfonic acid groups, which are capable of forming salts with alkali; or potentially acid-yielding groups such as anhydrides or lactones. Preferably the acid polymer contains free carboxyl groups. Alternatively, the acid-reacting reagent may be in a layer adjacent the silver halide most distant from the image-receiving layer, as disclosed in U.S. Pat. No. 3,573,043 issued Mar. 30, 1971 to Edwin H. Land. Another system for providing an acid-reacting reagent is disclosed in U.S. Pat. No. 3,576,625 issued Apr. 27, 1971 to Edwin H. Land.

An inert interlayer or spacer layer may be used in association with the polymeric acid layer to control or "time" the pH reduction so that it is not premature and interfere with the development process. Suitable spacer or "timing" layers useful for this purpose are described with particularity in U.S. Pat. Nos. 3,362,819; 3,419,389; 3,421,893; 3,455,686; and 3,575,701.

As is now well known and illustrated, for example, in the previously cited patents, the liquid processing composition referred to for effecting multicolor diffusion transfer processes comprises at least an aqueous solution of an alkaline material and possesses a pH of at least 12. Preferably, the alkaline material employed in the subject invention, is an alkali metal hydroxide.

The processing composition also preferably includes a viscosity-imparting reagent constituting a film-forming material of the type which, when the composition is spread and dried, forms a relatively firm and relatively stable film. This reagent may be a cellulosic polymer, for example, hydroxyethyl cellulose or sodium carboxymethyl cellulose; an oxime polymer, for example, polydiacetone acrylamide oxime; or other alkali-stable high molecular weight polymer. The viscosity-imparting reagent is preferably contained in the processing composition in such suitable quantities as to impart to the composition a viscosity in excess of 100 cps. at a temperature of approximately 24° C. and preferably in the order of 100,000 cps. to 200,000 cps. at that temperature.

As mentioned previously, a light-absorbing pH-sensitive optical filter agent which absorbs in the shorter wavelength range of the visible spectrum, usually, an indole phthalein is used in combination with the subject phthaleins to provide further protection throughout the visible spectrum. As used herein, the term "indole phthalein" is intended to include both 3,3-di(indol-3-yl) phthalides and 3,3-di(indol-3-yl) naphthalides such as the phthaleins disclosed in aforementioned U.S. Pat. No. 3,702,244. Preferred indole phthaleins are those forming the subject matter of U.S. Pat. No. 4,615,966.

The pH-sensitive phthalein dye(s) employed as the light-absorbing optical filter agents preferably are initially contained in the processing composition in their colored form together with the light-reflecting material, for example, titanium dioxide. The concentration of phthalein dye is selected to provide the optical transmission density required, in combination with the other layers intermediate the silver halide emulsion layer(s) and the incident radiation, to prevent nonimagewise exposure, i.e., fogging by incident actinic light during performance of the particular photographic process. The transmission density and the concentration of phthalein dye necessary to provide the requisite protection from incident light may be readily determined for any photographic process by routine experimentation, as a function of film speed or sensitivity, thickness of opacification layer, processing time, anticipated incident light intensity, etc., as described in said U.S. Pat. No. 3,647,437. It will be recognized that a particular transmission density may not be required for all portions of the spectrum, lesser density being sufficient in wavelength regions corresponding to lesser sensitivities of the particular photosensitive material. As indicated above, it will be recognized that a mixture of phthalein dyes may be used to obtain absorption in all critical areas of the visible and near-visible by which the silver halide emulsions being used are exposable.

Where the light-absorbing phthalein optical filter agent is present in the processing composition, it is advantageous to utilize an image-receiving component having a surface layer adapted to decolorize the optical filter agent adjacent the interface between said component and the layer of processing composition. Suitable decolorizing layers are described in U.S. Pat. No. 4,298,674 of Edwin H. Land, Leon D. Cerankowski and Neil C. Mattucci, in U.S. Pat. No. 4,294,907 of Irena Bronstein-Bonte, Edward P. Lindholm and Lloyd D. Taylor and in U.S. Pat. 4,367,277 of Charles K. Chiklis and Neil C. Mattucci.

To further illustrate the present invention, the optical transmission density of the compound of Example 1 at a concentration of $1\times10^{-4}$ in 1N aqueous potassium hydroxide solution was measured spectrophotometrically over the wavelength range of 350 nm to 800 nm. The resulting curve designated Curve 1 is shown in the FIGURE. As a comparison, the transmission density of a di-(o-carboxynaphthol) phthalein (Compound C) was measured in the same manner and at the same concentration in 1N aqueous potassium hydroxide solution. The resulting curve is designated Curve C in the FIGURE.

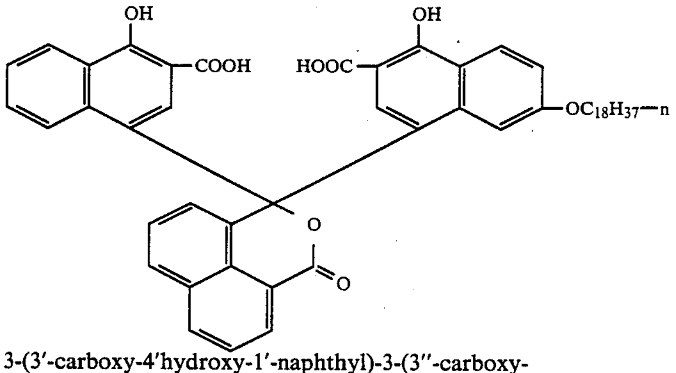

Compound C 3-(3'-carboxy-4'hydroxy-1'-naphthyl)-3-(3"-carboxy-4"-hydroxy-7"-octadecyloxy-1"-naphthyl)naphthalide As can be seen from reference to the FIGURE, the phenanthrol/o-carboxynaphthol phthaleins of the present invention as compared to di-(o-carboxynaphthol) phthaleins absorb more strongly in the red and near infrared region of the visible spectrum. The λmax and absorption measured at the λmax (Epsilon) was 662 nm (E=17,000) for the compound of Example 1 as compared to 650 nm (E=14,600) for Compound C. The optical transmission density for the compound of Example 2 was measured in the same way, and it was found that the spectral curve was similar to that of Example 1.

It will be understood that this invention is applicable to a wide variety of photographic processes employing any of various image-providing materials and that the transfer image may be in silver or in dye. Since such processes are now well known, it is not necessary to describe them in detail.

It will be understood that in any of these photographic systems, the transfer image may be positive or negative with respect to the photographic subject matter as a function of the particular image-forming system and that the silver halide emulsion may be negative-working or positive-working. Likewise, the image-receiving layer or other layers of the negative and positive components may vary as appropriate for a given process.

Since certain changes may be made in the above subject matter without departing from the scope of the invention herein involved, it is intended that all matter contained in the above description or shown in the accompanying drawing shall be interpreted as illustrative and not in a limiting sense.

I claim:

1. In a photographic film unit adapted for forming a transfer image viewable as a reflection print including a negative component comprising a photosensitive silver halide emulsion carried on a support; a positive component comprising an image-receiving layer carried on a transparent support; an acid-reacting layer disposed in at least one of said negative and positive components; and an aqueous alkaline processing composition comprising a light-reflecting pigment and at least one light-absorbing, pH sensitive optical filter agent releasably contained in a rupturable container positioned to release said composition for distribution between said negative and said positive components, the combination of said light-reflecting pigment and said optical filter agent being effective to prevent further exposure of said photosensitive emulsion during processing in the presence of radiation actinic to said emulsion and said light-reflecting pigment providing a layer after development which is effective to mask said photosensitive layer and provide a background for viewing the transfer image by reflected light;

the improvement which comprises employing as said processing composition, an aqueous alkaline solution comprising a light-reflecting pigment and as at least one said light-absorbing pH-sensitive optical filter agent, a pH-sensitive phthalein of the formula

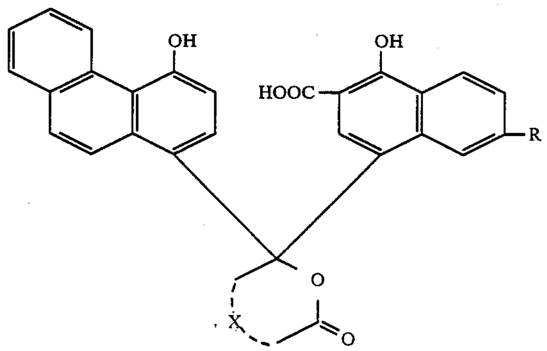

wherein R is alkoxy having at least 12 carbon atoms and X represents the carbon atoms necessary to complete phthalide or naphthalide.

2. A photographic film unit as defined in claim 1 wherein X completes naphthalide.

3. A photographic film unit as defined in claim 2 wherein said R contains 12 to 24 carbon atoms.

4. A photographic film unit as defined in claim 1 wherein said processing composition additionally includes a viscosity imparting reagent.

5. A photographic film unit as defined in claim 1 wherein said light-reflecting pigment is titanium dioxide.

6. A photographic film unit as defined in claim 1 wherein said processing composition includes a light-absorbing, pH-sensitive indole phthalein optical filter agent.

7. In a photographic process for forming a diffusion transfer image viewable as a reflection print which includes the steps of applying a layer of aqueous alkaline processing composition comprising a light-reflecting pigment and at least one light-absorbing pH-sensitive optical filter agent between a negative component comprising an exposed silver halide emulsion carried on a support and a positive component comprising an image-receiving layer carried on a transparent support; said layer of processing composition being effective to develop said exposed silver halide emulsion and to form a visible image in said image-receiving layer and being effective to prevent transmission of light actinic to said silver halide emulsion during development thereof; and after a predetermined time, reducing the pH of said processing composition layer to a pH effective to decolorize said pH-sensitive optical filter agent; said pH reduction being effected by an acid-reacting layer disposed in at least one of said negative and positive components;

the improvement which comprises applying as said processing composition layer, an aqueous alkaline solution comprising a light-reflecting pigment and as at least one said light-absorbing pH-sensitive optical filter agent, a pH-sensitive phthalein of the formula

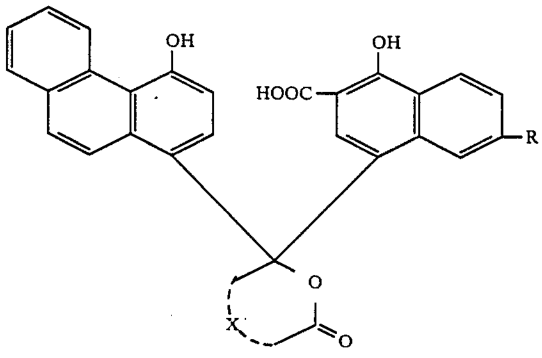

wherein R is alkoxy having at least 12 carbon atoms and X represents the carbon atoms necessary to complete phthalide or naphthalide.

8. A photographic process as defined in claim 7 wherein said X completes naphthalide.

9. A photographic process as defined in claim 8, wherein said R contains 12 to 24 carbon atoms.

10. A photographic process as defined in claim 7 wherein said processing composition additionally includes a viscosity-imparting reagent.

11. A photographic process as defined in claim 7 wherein said light-reflecting pigment is titanium dioxide.

12. A photographic process as defined in claim 7 wherein said processing composition includes a light-absorbing, pH-sensitive indole phthalein optical filter agent.

13. A rupturable container for use in diffusion transfer film units adapted to provide transfer images viewable by reflected light, said rupturable container releasably holding an aqueous alkaline processing composition comprising an aqueous solution of alkali metal hydroxide, a light-reflecting pigment and at least one light-absorbing, pH-sensitive optical filter agent, at least one said optical filter agent being a pH-sensitive phthalein of the formula

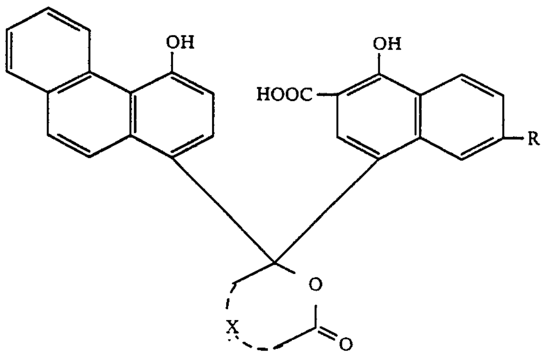

wherein R is alkoxy having at least 12 carbon atoms and X represents the carbon atoms necessary to complete phthalide or naphthalide.

14. A rupturable container releasably holding an aqueous alkaline processing composition as defined in claim 13 wherein said X completes naphthalide.

15. A rupturable container releasably holding an aqueous alkaline processing composition as defined in claim 13 wherein said R contains 12 to 24 carbon atoms.

16. A rupturable container releasably holding an aqueous alkaline processing composition as defined in claim 13 wherein said processing composition additionally includes a viscosity-imparting reagent.

17. A rupturable container releasably holding an aqueous alkaline processing composition as defined in claim 13 wherein said light-reflecting pigment is titanium dioxide.

18. A rupturable container releasably holding an aqueous alkaline processing composition as defined in claim 13 wherein said processing composition includes a light-absorbing, pH-sensitive indole phthalein optical filter agent.

19. A compound having the formula

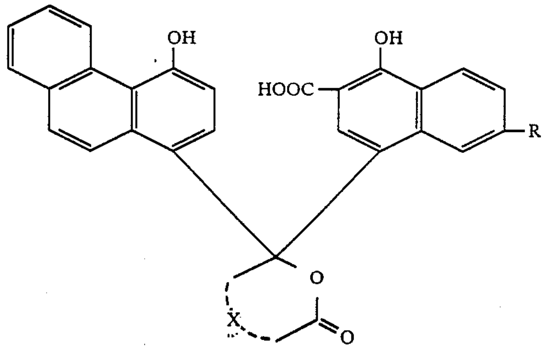

wherein R is alkoxy having at least 12 carbon atoms and X represents the carbon atoms necessary to complete phthalide or naphthalide.

20. A compound as defined in claim 19 wherein X completes naphthalide.

21. A compound as defined in claim 19 wherein said R contains 12 to 24 carbon atoms.

22. A compound as defined in claim 19 wherein said R contains 12 carbon atoms.

23. A compound as defined in claim 19 wherein said R contains 18 carbon atoms.

* * * * *